(12) United States Patent
Montgomery

(10) Patent No.: US 9,272,058 B1
(45) Date of Patent: Mar. 1, 2016

(54) SANITIZING DEVICE, SYSTEM AND METHODS OF USE THEREOF

(71) Applicant: Michael W. Montgomery, Decatur, GA (US)

(72) Inventor: Michael W. Montgomery, Decatur, GA (US)

( * ) Notice: Subject to any disclaimer, the term of this patent is extended or adjusted under 35 U.S.C. 154(b) by 0 days.

(21) Appl. No.: 14/215,106

(22) Filed: Mar. 17, 2014

Related U.S. Application Data

(60) Provisional application No. 61/801,246, filed on Mar. 15, 2013.

(51) Int. Cl.
*A61L 2/26* (2006.01)
*A61L 2/00* (2006.01)

(52) U.S. Cl.
CPC *A61L 2/0047* (2013.01); *A61L 2/26* (2013.01)

(58) Field of Classification Search
USPC .......................................... 250/455.11, 504 H
See application file for complete search history.

(56) References Cited

U.S. PATENT DOCUMENTS

| | | | | |
|---|---|---|---|---|
| 8,470,239 B1* | 6/2013 | Kerr | ........................ | A61L 2/10 422/22 |
| 2006/0057020 A1* | 3/2006 | Tufo | ........................ | A61L 9/20 422/24 |
| 2008/0310996 A1* | 12/2008 | Kim et al. | ........................ | 422/24 |
| 2010/0193709 A1* | 8/2010 | Dalton | ...................... | 250/504 R |

FOREIGN PATENT DOCUMENTS

| | | | |
|---|---|---|---|
| ES | WO 2009147264 A1 * | 12/2009 | ........... A43B 1/0045 |
| WO | WO 2009147264 A1 * | 12/2009 | |

OTHER PUBLICATIONS

J. Barker, D. Stevens, and S.F. Bloomfield, Spread and Prevention of Some Common Viral Infections in Community Facilities and Domestic Homes, Journal of Applied Microbiology 2001, vol. 91, pp. 7-21.
Guardian Technologies, www.guardiantechnologies.com/catalogsearch/result/?q=uv+sanitizer,10 pages.
Purelyuv, www.purelyuv.com/uv-bulbs/puvh2311-g23-11-watt.aspx, 2 pages.
Verilux, www.verilux.com/uv-products/uvc-sanitizing-wand, 3 pages.
Verilux, www.verilux.com/replacement-bulbs/uvs-wand-replacement-bulb, 1 page.

* cited by examiner

*Primary Examiner* — Phillip A Johnston
*Assistant Examiner* — Hsien Tsai
(74) *Attorney, Agent, or Firm* — Nora M. Tocups

(57) ABSTRACT

A device that eliminates contaminants before they can be transmitted throughout a structure. The device may include a platform housing a disinfection source for selectively emitting UV-C light. The platform has a top. The top has two areas that pass the UV-C light with the remaining area of the top unable to pass the UV-C light. The two areas of the top are capable of supporting a person standing on the areas with a foot respectively on each area. The disinfection source is configured to emit the UV-C light when a person stands on the two areas, but not when there is no person standing on the two areas. The disinfection source may be removable from the platform for use in disinfecting objects.

7 Claims, 2 Drawing Sheets

SANITIZING DEVICE, SYSTEM AND METHODS OF USE THEREOF

RELATED APPLICATION

This application claims priority to and the benefit of the prior filed and commonly owned provisional application entitled "SANITIZING DEVICE, SYSTEM AND METHODS OF USE THEREOF", which was filed with the United States Patent and Trademark Office on Mar. 15, 2013, assigned U.S. Patent Application Ser. No. 61/801,246, and is incorporated herein by this reference.

FIELD OF THE INVENTION

The invention relates to sanitizing devices, systems, and methods of use thereof.

BACKGROUND

It has long been known that indoor pollution is one of mankind's major health concerns, and as people spend more and more time indoors, cleanliness of that environment becomes increasingly important. Citations to several of the studies of these indoor environments, and quotes from these studies follow. "Viruses are probably the most common cause of infectious disease acquired within indoor environments and have considerable impact on human health ranging from severe life threatening illness to relatively mild and self limiting or asymptomatic diseases. In particular, viruses causing gastrointestinal and respiratory diseases spread rapidly in the community and can cause considerable morbidity". J. Barker, D. Stevens, S. F. Bloomfield, *Spread and Prevention of Common Viral Infections*, Volume 91, Issue 1, Pages 7-21, July 2001. "Viruses are the causative agents of an estimated 60% of human infections worldwide. Transmission of these viruses from an infected person to a new host can occur via several routes." P. Vasikova, I. Pavlik, M. Verani, A. Carducci, published online Feb. 4, 2010, Springer Science and Business Media, LLC. Both of the articles cited in this paragraph are incorporated herein by reference.

Recent studies by Charles Gerba (University of Arizona; 2008), in association with Rockport Shoes, have shown that the soles of shoes are one of the main entry sources of these pollutants into the indoor environment. Some of the more common contaminants found on shoe soles are *Escherichia Coli* (*E. Coli*), which causes kidney failure, gastrointestinal infections, urinary tract infections, meningitis and death in 1 out of 50 patients, oftentimes originating from the floors of public restrooms or animal fecal matter; *Klebisiella Pneumonia*, which causes and pneumonia and death in 25% to 50% of patients by destroying lung tissue, as well as secondary wound and bloodstream infections and *Serratia Ficaria*, which causes damage to the gall bladder. The studies by Charles Gerba also showed that the frequency of bacterial transfer from shoe to uncontaminated surfaces ranged from 90%-99%. These contaminants include the aforementioned viruses and bacteria, as well as dust mites and other pathogens. The Gerber studies are incorporated by reference.

SUMMARY

Stated generally, the invention relates to devices, system, and methods for sanitizing. For example, a first embodiment is a device that eliminates contaminants before they can be transmitted throughout a structure. This first embodiment includes a platform housing a disinfection source for selectively emitting UV-C light. The platform has a top. The top has two areas that pass the UV-C light with remaining area of the top unable to pass the UV-C light. The two areas of the top that pass the UV-C light are capable of supporting a person standing on the areas with a foot respectively on each area. A disinfection source emits the UV-C light when the person stands on the two areas, but not when no person stands on the two areas. The disinfection source may be removable from the platform for use in disinfecting objects.

A second embodiment is a system for disinfecting items. It includes a housing having a top area able to pass UV-light. The housing has space underneath the top to receive and support a wand capable of selectively emitting the UV light. The housing has walls for supporting the top and for blocking transmission of the UV light when the wand emits the UV light.

The second embodiment also includes a first mat having at least an area of a first size for passing the UV-light. The remaining area of the first mat is unable to pass the UV-light. The second embodiment also includes a second mat that has at least an area of a second size for passing the UV-light. The other area of the second mat is unable to pass the UV-light.

In this second embodiment, the wand is selectively removable from the housing for disinfecting objects. A switch is provided for selectively activating the wand to emit the UV-C light and deactivating the wand to not emit the UV-C light.

A third embodiment of the invention is an apparatus for sanitizing one or more items. It includes a box having a top able to transmit disinfecting rays. The third embodiment also includes a mat for placement on top of the box. The mat has two shoe sole shaped areas that transmit the disinfecting rays with remaining area of the mat blocking the disinfecting rays.

The third embodiment includes a source for emitting the disinfecting rays housed within the box. The box and its top are capable of supporting a person who steps onto the two shoe sole shaped areas of the mat on the top of the box. The source emits the disinfecting rays when the person steps onto the two shoe sole shaped areas of the mat on the top of the box. The source halts the disinfecting rays when the person steps off the two shoe sole shaped areas.

The third embodiment may include two mats. The two shoe sole shaped areas in the first mat are of a first size. The two shoe sole shaped areas in the second mat are of a of a size different from the first size two shoe sole shaped areas of the first mat.

Other features and advantages of the invention may be more clearly understood and appreciated from a review of the following detailed description and by reference to the appended drawings and claims.

DETAILED DESCRIPTION

The invention is described herein at least in sufficient detail for a person skilled in the art to make or use the invention without undue experimentation. The invention is described by reference to exemplary embodiments including apparatuses, systems, and methods. The invention, however, should not be limited to the embodiments described herein, but also may cover other embodiments (not specifically described or shown herein) that may be implemented in accordance with the inventions.

Figure 1:
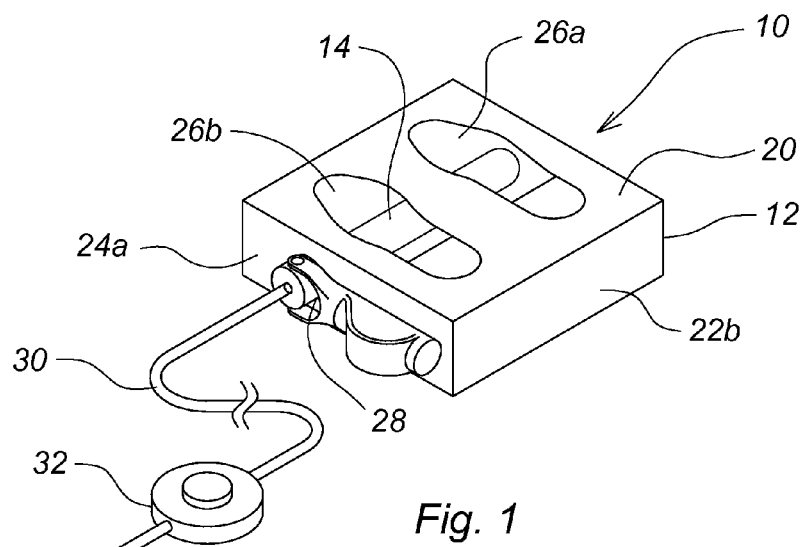
FIG. 1 is a top perspective overview of an exemplary embodiment of the invention.
Figure 1:
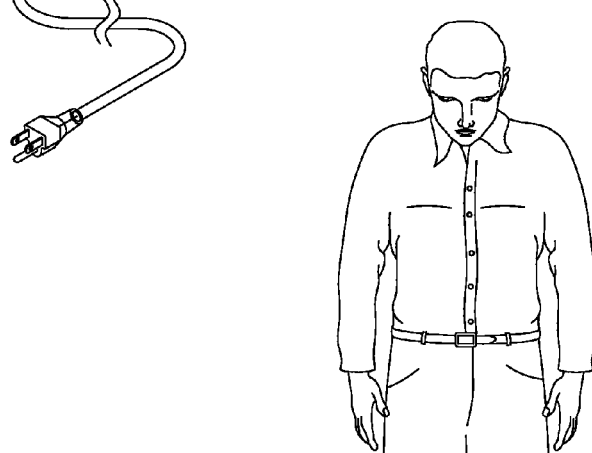

The invention may be embodied in a variety of ways. FIG. 1 illustrates just one example. It is a device 10 including a platform 12 housing a source 14 that disinfects. The platform 12 also may be referred to herein as the "housing" or "box". Device 10 may be strategically placed and easily accessed for disinfecting items such as the soles of shoes. For example, the device 10 may be placed at a user-selected point of entry.

Figure 2:
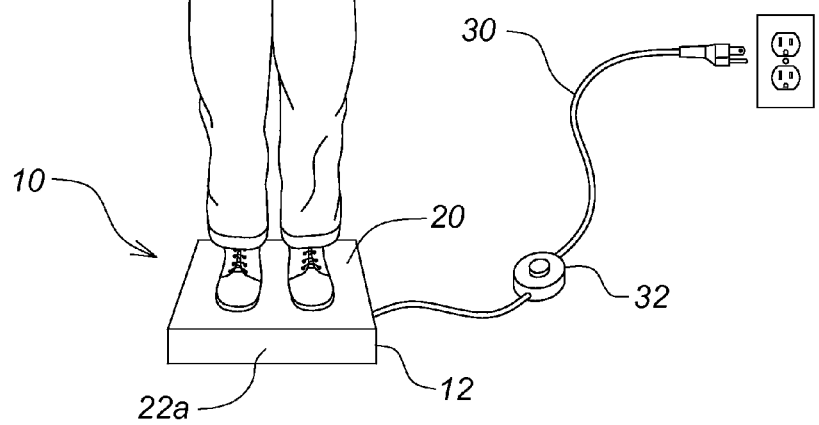
FIG. 2 shows an exemplary embodiment of the invention in use with a user.

FIG. 2 illustrates the device 10 in use. To disinfect the bottom of his or her shoes, the user may step onto the top 20 of the platform 12 of the device 10. The top 20, in this embodiment, includes two areas 26a, 26b that pass UV-C light. The remaining area outside the two areas 26a, 26b of the top 20 does not pass UV-C light. Thus, when the user steps onto the top 20 of the device 10, he or she may position his or her feet over the areas 26a, 26b. The user then activates the disinfecting source 14 (or it may automatically activate). In response, the source 14 disinfects the bottom of the user's shoes. The user may have to wait a few seconds while the disinfection process is completed. After enough time has elapsed for disinfection, the device 10 may automatically turn-off the disinfecting source 14 or the user may deactivate it. The user then may step off the device 10 with the bottom of his or her shoes disinfected.

Advantageously, use of the device 10 in doorways substantially eliminates the contaminants at points of entry before they can be brought into and transmitted throughout a structure or other limited environment.

Exemplary embodiments of the invention may provide one or more mats to be used as the top 20 of the device 10 or to be used with the top 20. Each mat may include an area(s) that pass(es) UV-C light. The areas on some of the mats may be configured respectively to reflect different shoe sizes or shapes. A family using the device 10 might select a mat according to the most common shoe size among family members, or could switch out mats to accommodate a wide range of sizes. Such use of a mat with the exemplary device may have at least two-fold purposes. The mat may aid in the positioning of the feet. Also the mat may block some of the UV-C light so as to minimize the user's concerns about exposure to UV-C light that would otherwise escape from the portion of the top not covered by the item, or items, being sanitized.

Another advantage of the device 10 and like embodiments of the invention is that the device 10 may be used to sanitize or disinfect items other than the bottoms of shoes. In fact, the top 20 of the box 12 may be considered a platform upon which a user may place, and disinfect, other of the many items which have been identified as carriers of germs such as cellphones, remote controls, dishrags, sponges and purses, to name but a few. To carry out such disinfection, a user simply places the item to be cleaned on the area(s) of the top 20 of the box 12, where the UV-C light is passed through. The user activates the device 10, and UV-C light is emitted from the source 14 and passes through the top 20 of the box 12 to the underside of the item placed on top 20 of the box 12. After a period of time of UV-C light emission, enough to disinfect the item, the UV-C light emitter is de-activated (automatically or manually). The item is disinfected and may be removed from the top 20 of the device 10.

To facilitate the disinfection of items other than the bottoms of shoes, a variety of tops or adaptors for the exemplary device 10 may be made available to users. Each of the tops or adaptors may have differently shaped area(s) that pass UV-C light. For example, to disinfect a small item without risking extra exposure to UV-C light, a user may choose to use a top or adaptor with an area that passes UV-C light that is just big enough to pass only as much UV-light as is necessary to disinfect the small item. For relatively quick disinfection of larger items, a user may choose to use a top with a bigger area(s) that passes UV-C light. Alternatively, the user may use the top or an adaptor with the smaller area that passes UV-C light for disinfection of the larger item. In that case, however, the user may have to run several courses of disinfection—each time positioning a non-disinfected area of the larger item over the smaller area that passes UV-C light until the entire larger item has been disinfected.

Further, the exemplary device might be made available with one or more mats that fit as the top 12 or may be made to fit onto the top 20 of the box 12. The mats respectively may have a wide assortment of sized and/or shaped areas that pass UV-C light. One mat at a time may be used with the device 10, or more than one mat may be configured with the device. Thus, the mats may be the same size as the top 20 of the device 10 or may be of varying sizes.

For example, assume a user desires to disinfect four relatively small items. To most efficiently carry out the disinfection, the user may use four mats where each mat is about ¼th the size of the top 12 of the box 10, and where each mat has an area about the size of the small items to be disinfected. The user positions the four mats on the top 12 of the box 10, places each of the items onto the respective areas of the mats that pass UV-C light, and then engages the UV-C light bulb. All four items are disinfected at the same time.

In the exemplary device 10, the source that is used for the substantial elimination of contaminants is an ultra-violet (UV) light bulb. Other or additional means may be used as disinfecting source 14. With respect to the ultra-violet light bulb, it emits the shorter wavelengths of the ultraviolet spectrum. Ultraviolet light is invisible to the eye and has wavelengths that range from 100 to 400 nanometers (nm). The ultraviolet spectrum is further divided into UV-A, UV-B, and UV-C. UV-C light, at 254 nanometers, has been proven to be an effective germicidal by destroying the deoxyribonucleic acid (DNA) of bacteria, viruses and other pathogens. The destruction prevents the target organism from multiplying and causing disease.

FIGS. 1 and 2 depict the exemplary embodiment 10 as a box upon which a user may step up on to disinfect his or her shoes. Other configurations of the invention are possible. For example, the box-like embodiment 10 may be made to fit into the flooring in front of a door or other location for disinfection. By such a fit into the flooring, a user does not have to step up onto a box including the invention. Instead, the user may simply step to the correct location in the floor for disinfection. As another example, an embodiment does not provide a box like in FIGS. 1 and 2, but instead, the elements are made to fit with flooring such as an area in front of a door. These alternate embodiment do not contemplate the removal of the disinfecting source 14 for disinfection other than the floor location.

Figure 3:
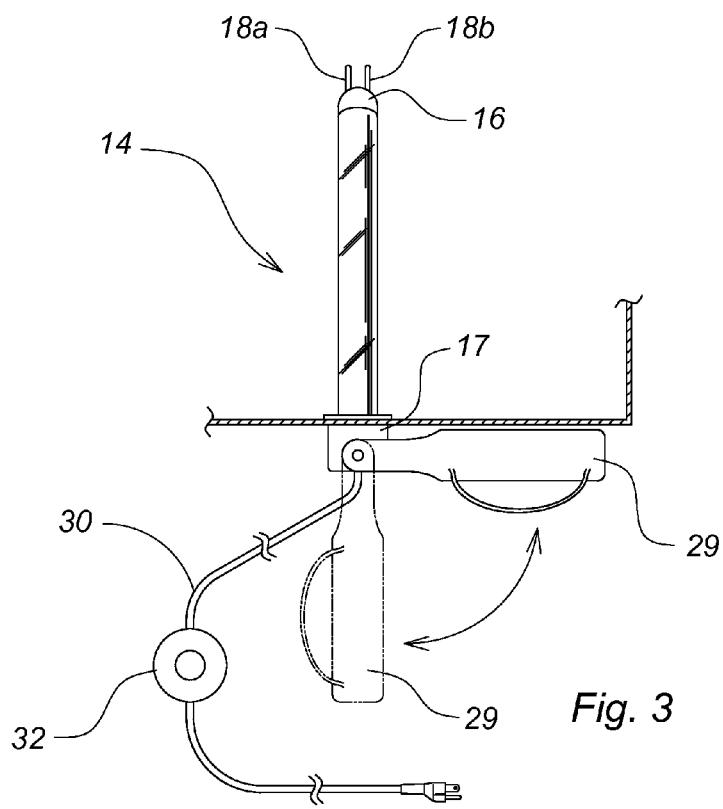
FIG. 3 shows a side view of a wand as may be used with the exemplary embodiment of FIG. 1.

FIG. 3 provides a more detailed view of the disinfecting source 14 of the exemplary device 10. The source 14 for disinfection is a UV-C light bulb having a generally tubular shape. The bulb 14 is about ten inches long and one inch in diameter. At a distal end 16 of the bulb 14, two pins 18a, b are disposed on the bulb 14 to hold it in place by means of a bulb framework comprising electrical and structural elements inside the housing 12 (not shown). The use of two pins 18a, 18b to hold the bulb 14 in place in the housing 12 is comparable to the mechanism typically used with fluorescent bulbs such as are often installed under upper kitchen cabinets to provide light on a kitchen counter.

The UV-C light bulb 14 used in the exemplary device 10 is generally available from any number of manufacturers and suppliers. Such bulbs may be similar to the VHRB01 from the Verilux Co. or the PUVH2311 from Purely Products. These bulbs are examples of the possible sizes and shapes of the bulbs, but the invention should not be limited only to the use of these bulbs. A UV-C bulb 14 provided with an exemplary device 10 when purchased may eventually burn out. Advantageously, the bulb 14 is easily replaced by the consumer.

In the exemplary device 10, the UV-C light emitting bulb 14 is contained in a platform 12 that is shaped as a relatively low profile box. The shape of the platform may vary from embodiment to embodiment. The invention should not be limited to a box-like platform 12.

The platform 12 may be sized to house the UV-C light source 14 and provide an area(s) of appropriate size on its top 20 to accommodate the item(s) to be disinfected. In the illustrated embodiment, the box 12 is approximately 12 inches by 12 inches square and 4-5 inches high. As a substantially square box 12, it has a top 20 and four supporting sides 22a, 22b, 24a, and 24b. The front side 22a of the box 12 is seen in FIG. 2, and its parallel back side 22b is seen in FIG. 1. The other two sides (only left side 24a is visible in the drawings) are generally parallel to each other and generally perpendicular to the front and back sides 22a, 22b.

The platform 12 of the exemplary device 10 may be constructed of one or more materials capable of supporting a weight in line with the intended use of the device 10. For example, if an embodiment is intended to be used by adults of average weight, then the box 12 must support that weight when the adult steps onto the top 20 of the box 12. Heavy plastic or other material(s) may be used in whole or in part. The sides 22a, 22b and 24a, 24b may be made of the same material as the top 20 in whole or in part or not.

In the exemplary device 10, the top 20 of the box 12 differs from the remainder of the box 12 at least insomuch as the top 20 (or portions thereof) has two areas 26a, 26b that pass the UV-C light emitted by the bulb 14. The two areas 26a, 26b pass the UV-C light so that the bottom surface of items placed on the two areas 26a, 26b (such as the bottom of a pair of shoes) may be disinfected by the UV-C light source 14. One or both of the two areas 26a, 26b may be made integrally with the remainder of the top 20 of the device, or otherwise. The two areas 26a, 26b may be made of any material(s) that support(s) the weight of intended items or persons for disinfection and that passes UV-C light. The two areas 26a, 26b need not look different from the rest of the top 20 of the box 12, or they may look different as in the illustrated embodiment 10. For example, the areas 26a, 26b may be further transparent so as to allow a user to see through the areas 26a, 26b.

An alternative embodiment may have a platform top that is completely transparent to UV-C light. There may be a drawback to having the whole top of a platform being transparent to UV-C light. Assume a stuffed animal is put on top of such a platform for disinfection. Also assume the stuffed animal does not completely cover the whole transparent top of the platform. When the UV-C light source is turned on, UV-C light disinfects the part of the stuffed animal that is placed on top of the platform. Additional UV-C light passes through the top of the platform around the stuffed animal. If there is something in the path of the UV-C light, it will be exposed to the UV-C light. That exposure may or may not be harmful depending on the nature of the "something" and the distance it is from the UV-C light source.—

Referring again to the exemplary embodiment 10 shown in the diagrams, the two areas 26a, 26b on the top 20 of the platform 12 are shaped like corresponding shoe prints. The shoe prints 26a, 26b are transparent to UV-C light to allow for disinfection of whatever is placed on top of them when the device 10 is activated. One or both of the shoe prints 26a, 26b also may be transparent so that a user may see through the one or both. One or both of the shoe prints 26a, 26b may have writing or decorations on them that contrast with the surrounding material but are also transparent to UV-C light. As an example, the right shoe print 26a may be labeled "Right" in writing applied by contrasting UV-C transparent material, and the left 26b may be labeled "Left" in the same writing material. Such writing may teach a young child to tell his or her right from his or her left.

FIG. 1 shows two shoe prints 26a, 26b in the top 20 of the exemplary device 10. The shoe prints 26a, 26b in this embodiment correspond generally to the shape of the bottom of a pair of men's shoes. A user wearing such shoes may step onto the top 20 of the device 10 and position his feet on the cut-outs 26a, 26b. Advantageously, the shoe prints 26a, 26b may function as aids to positioning feet, shoes, and other objects to be disinfected on the top 20 of the device 10.

The user's shoes may not cover the entire area of the shoe prints 26a, 26b and some UV-C light may pass through the area(s) of shoe prints 26a, 26b that are not covered. The small amount of UV-C light to which the user is exposed by the light that passes through the uncovered area(s) is not believed to be enough to be dangerous or otherwise a concern.

Alternatively, the user's shoes may cover more of the top 20 of the platform 12 than just the shoe prints 26a, 26b. In that case, the user may have to engage in more than one disinfection session with the device 10. The user may have to shift the positions of his or her shoes on the shoe prints 26a, 26b for each session until the entire bottoms of the shoes are disinfected or at least as much of the bottoms are disinfected as the user desires. The same process may need to be followed if a user desires to disinfect an item larger than the areas of the shoe prints 26a, 26b.

The invention, however, should not be limited to areas 26a, 26b that are shaped like the bottom of men's shoes. Other shapes and sizes may be used in addition or in the alternative. Another embodiment may have a single area, or more than two areas that pass UV-C light. When more than one area is used in an embodiment, they do not necessarily have to be the same shape or size or have the same decoration.

As noted, in the exemplary device 10, the remaining portion of the top 20 other than the areas 26a, 26b may be made of a material or otherwise constructed so that UV-C light does not pass through. In that case, another function of the top 20 with areas 26a, 26b is to prevent UV-C light from being transmitted through the top 20 except through the areas 26a, 26b. Thereby, the user may be saved from exposure to more UV-C light than is necessary to disinfect his or her shoes. Yet another function of the areas 26a, 26b may be to aid in decorating the device 10. Also in the exemplary embodiment 10, one or more of the platform's 12 four sides 22a, 22b, 24a, and 24b may be made of a material(s) that do/does not pass UV-C light. By having one or more sides 22a, 22b, 24a, and 24b that do not pass UV-C light, the amount a user and/or other nearby persons or items is exposed to UV-C light is less than if the all of the sides were transparent to UV-C light.

The exemplary device 10 may be made available in different colors, for example black, light brown or white, so that the device 10 appears less machine-like and blends more effectively with the surroundings. The areas 26a, 26b of the exemplary device 10 may be without color or may be of one or more colors so long as the areas pass UV-C light. The areas 26a, 26b do not have to be the same color or be decorated the same as the rest of the device 10, but they could be.

The top 20 of the device 10 may differ from the remaining elements of the box 12 in color, in material, in decoration, etc. A device according to the invention may be sold with more than one top or with adaptors so as to facilitate specific disinfection of men's shoes as compared to women's or children's shoes, or other items. Such specific tops or adaptors may be each sold separately.

Explanation is now provided as to the positioning of the UV-C light bulb 14 in the box 12 of the exemplary device 10. The box 12 is substantially hollow prior to insertion of the bulb 14. It may be inserted into an opening 28 generally centered in the left side 24a of the box 12. The bulb 14 may be inserted until the first inserted end 16 of the bulb 14 reaches its position on the inside right side 24b (not shown) of the box 12. The pins 18a, 18b on that end 16 of the bulb 14 may be made to fit or mate with appropriate elements positioned on the inside right side 24b of the box 12.

After insertion, the last inserted end 17 of the bulb 14 may rest in or on the opening 28 in the left side 24a of the box 12, or otherwise be configured. The bulb 14 may be permanently fixed in the box 12, or as explained in more detail, may be positioned so as to be readily removable for other disinfection uses.

Figure 4:
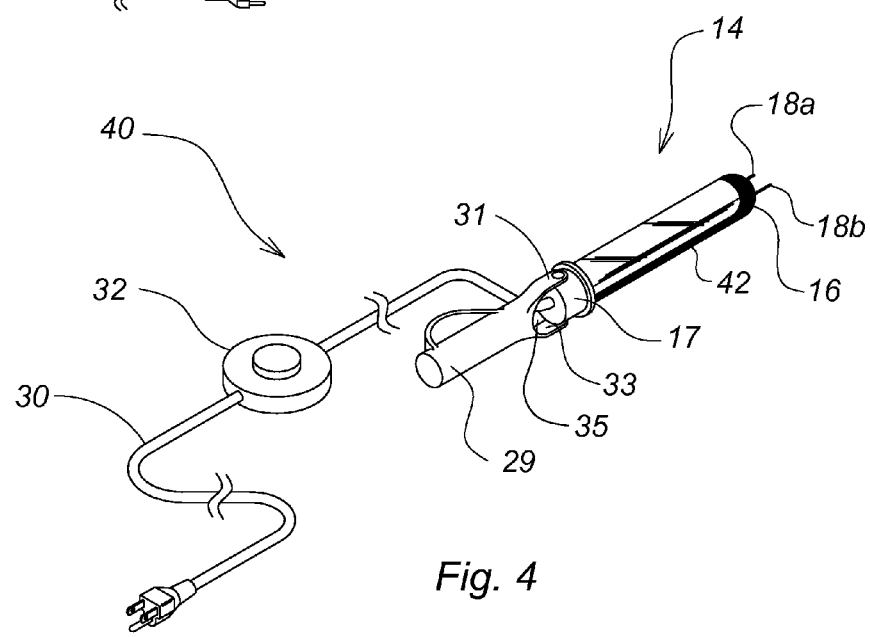
FIG. 4 is a top perspective overview of a wand as may be used with the exemplary embodiment of FIG. 1.

Another advantage of the exemplary device 10 is that its UV-C light bulb 14 may be removed from its box 12 to be used as a portable sanitizer 40. See FIG. 4. Bulb 14 may be installed in a frame, or wand, comprising the bulb and a handle 29 incorporating a portable power source, such as a battery, or to which a power cord is attached. Such a wand would be removable from the box 12 as a unit and used in sanitizing objects or surfaces away from the box itself. The handle 29 (see FIG. 4) may be made to project beyond the side of the box and may allow the user to remove the wand by grasping the handle 29 and sliding the wand horizontally out of the box. The bulb 14 is then portable and can be used by means of the wand to sweep any areas of concern to the user such as countertops, entry mats, mattresses or pillows. The wand may also incorporate a shade 42, corresponding generally to at least part of the shape and size of the bulb, which may direct and focus the sanitizing UV-C light while isolating the user from exposure to the UV-C light. When the disinfection of such objects or surfaces away from the box is complete, the bulb, in its shade, is re-inserted into the box, and the handle 29, which may be hinged (see FIG. 3), is folded against the side of the box, and out of the way.

When inserted into the box 12, the bulb's 14 entire length (substantially) is contained within the box 12. The bulb 14 spans the width of the box 12 from the left side 24a to the right side 24b. To start the disinfection process, a person using the device 10 steps onto the box 12 so his or her feet are generally perpendicular to the position of the light bulb 14 within the box 12. As noted above, the top 20 of the box 12 may include areas 26a, 26b to aid the user in such positioning. If an item other than the bottom of a pair of shoes is to be disinfected, the item may be placed generally perpendicular to the position of the light bulb 14 within the box 12 for disinfection. In an alternative embodiment, the bulb 14 may be differently positioned within the housing 12.

Embodiments of the invention may be powered in any appropriate way. The exemplary device 10 is powered by regular household current with a power cord 30 attached to the end 17 of the UV-C light bulb 14 opposite to its insertion end 16.

Advantageously, the power cord 30 cooperates with the handle 29 attached to the light bulb 14. In particular, as previously described, the handle 29 has two arms 31, 33 that extend from its main body to connect to the end 17 of the light bulb 14. The arms 31, 33 are disposed substantially opposite to each other on the end 17 of the bulb 14. Further, the arms define an opening 35 between the end 17 of the bulb 14 and the main body of the handle 29. The power cord 30 may pass through that opening to allow for connection of the power cord to the power source without interference with the handle whether the handle is in the open position or the closed position.

Plugging the power cord 30 into an outlet may be one way to power on an exemplary device according to the invention. In the exemplary device 10, however, the power cord 30 includes a switch 32, which may be made to lay flat on the floor or other surface. In other embodiments, the switch may be a simple on/off switch. In the exemplary device 10, the switch 32 is pressure sensitive. It may only be activated by a weight greater than that of an average child of eight years or about 75 lbs. The advantage of this pressure sensitive aspect of the switch 32 may prevent the UV-C light 14 from being activated by a curious toddler or roaming dog.

The switch 32 may include a timer (not shown in diagrams). The timer on the switch 32 may give the user a few moments' delay after stepping on the switch to allow the user time to get into position or place an item on the device 10. The timer turns the device 10 off when the sanitizing period is complete. This whole process might take approximately 10-12 seconds. In cases where the bulb is used in the portable application, the bulb can be activated continuously by constant pressure on the switch which overrides the timer until the sanitizing is complete, at which point the shade containing the bulb is re-inserted into the box.

Ideally, the exemplary device 10 is placed as close as possible to the entry point of a structure or an area the user desires to keep from contamination. The user approaches the device 10 and steps on the pressure sensitive switch. The switch 32 has a delay which allows the user time to position his/her shoes within the outlines provided on the top 20 of the box 12. The UV-C light bulb 14 activates for several seconds while the shoes are being sanitized. After several seconds, the timer on the switch 32 de-activates the light bulb 14. The user then may step off the box 12 and is free to enter the structure or area, stepping away from the area by which he/she entered, so as not to re-contaminate his/her shoes.

The exemplary device according to the invention is described above as including the features of the portable UV-C light wand, the feature of a sanitization device upon which a user may step and have his/her shoes sanitized or a platform upon which a user can place items for sanitization. Other embodiments of the invention may include only one or the other of the features. Yet other embodiments may include additional or different features.

In conclusion, it is reiterated that the exemplary devices according to the invention are described herein with reference to exemplary embodiments, alternative embodiments, and also with reference to the attached drawings. The invention, however, can be embodied into many different forms and carried out in a variety of ways, and should not be construed as limited to the embodiments set forth in this description and/or the drawings. The exemplary embodiments that are described and shown herein are only some of the ways to implement the inventions. Elements and/or actions of the inventions may be assembled, connected, configured, and/or taken in an order different in whole or in part from the descriptions herein.

I claim:

1. A device that eliminates contaminates before they can be transmitted throughout a structure, comprising:
    a platform housing a disinfection source for selectively emitting UV-C light;
    the platform having a top;
    the top having two areas that pass the UV-C light with remaining area of the top unable to pass the UV-C light, and the two areas of the top capable of supporting a person standing on the areas with a foot respectively on each area;
    the disinfection source emitting the UV-C light when the person stands on the two areas and the disinfection source not emitting the UV-C light when no person stands on the two areas; and
    the disinfection source including a bulb and a handle with the disinfection source being selectively removable by its handle from the platform for use in disinfecting objects.

2. The device of claim 1, wherein the handle is capable of being made to project beyond the platform so a user may selectively remove the disinfection source from the platform by grasping the projecting handle of the disinfection source.

3. A system for disinfecting items, comprising:
    a housing having a top area able to pass UV light,
    the housing having space underneath the top to receive and support a wand capable of selectively emitting the UV light, and
    the housing having walls for supporting the top and for blocking transmission of the UV light when the wand emits the UV light;
    a first mat having at least an area of a first size for passing the UV light with remaining area of the first mat unable to pass the UV light;
    a second mat having at least an area of a second size for passing the UV light with other area of the second mat unable to pass the UV light;
    the wand including a handle and a UV light source so the wand is selectively removable by its handle from the housing for disinfecting objects; and
    a switch for selectively activating the wand to emit the UV light and deactivating the wand to not emit the UV light.

4. An apparatus for sanitizing one or more items, comprising:
    a box having a top able to transmit disinfecting rays;
    a mat for placement on the top of the box with the mat having two shoe sole shaped areas that transmit the disinfecting rays with remaining area of the mat blocking the disinfecting rays;
    a source for emitting the disinfecting rays housed within the box;
    the box and top capable of supporting a person who steps onto the two shoe sole shaped areas of the mat on the top of the box;
    the source emitting the disinfecting rays when the person steps onto the two shoe sole shaped areas of the mat on the top of the box and the source halting the disinfecting rays when the person steps off the two shoe sole shaped areas; and
    the source including a handle so the source is selectively removable by its handle from the box for sanitizing one or more items.

5. The apparatus of claim 4 wherein the mat is a first mat and the two shoe sole shaped areas are of a first size; and
    further comprising a second mat with two shoe sole shaped areas of a size different from the first size two shoe sole shaped areas of the first mat.

6. The system of claim 3, wherein the handle of the wand is capable of being made to project beyond the housing wherein the handle is easy to grasp to remove the wand from the housing.

7. The apparatus of claim 4, the handle being capable of being made to project beyond the box so the source is removable by its handle from the box for sanitizing one or more items.

* * * * *